US 6,904,916 B2
Jun. 14, 2005

(12) United States Patent
Bakane

(10) Patent No.: US 6,904,916 B2
(45) Date of Patent: Jun. 14, 2005

(54) EXTERNAL INCONTINENCE DEVICE

(76) Inventor: Ramesh Bakane, 2030 W. Lola Dr., Marion, IN (US) 46952

( * ) Notice: Subject to any disclaimer, the term of this patent is extended or adjusted under 35 U.S.C. 154(b) by 78 days.

(21) Appl. No.: 10/382,451

(22) Filed: Mar. 6, 2003

(65) Prior Publication Data

US 2004/0173219 A1 Sep. 9, 2004

(51) Int. Cl.[7] .................................................. A61F 5/48
(52) U.S. Cl. ............................... 128/885; 128/DIG. 24; 600/29; 600/38
(58) Field of Search ................................ 128/885, 886, 128/DIG. 25; 600/29–31, 38, 41

(56) References Cited

U.S. PATENT DOCUMENTS

| | | | | |
|---|---|---|---|---|
| 2,756,753 | A | * | 7/1956 | Means ........................ 128/885 |
| 4,549,530 | A | | 10/1985 | Finney |
| D299,168 | S | | 12/1988 | Bergström et al. |
| 4,880,016 | A | | 11/1989 | Worth et al. |
| 5,336,157 | A | | 8/1994 | Hale |
| 5,415,179 | A | * | 5/1995 | Mendoza .................... 128/842 |
| 5,571,125 | A | | 11/1996 | Chadwick |
| 5,630,429 | A | | 5/1997 | Dann |
| 5,702,381 | A | | 12/1997 | Cottenden |
| 5,746,222 | A | | 5/1998 | Simon et al. |
| 5,842,968 | A | | 12/1998 | Johnson |
| 5,887,593 | A | | 3/1999 | Levius |
| 5,888,188 | A | | 3/1999 | Srougi et al. |
| 6,026,813 | A | | 2/2000 | Wilhelm |
| 6,026,816 | A | * | 2/2000 | McMillan et al. .......... 128/898 |
| 6,027,442 | A | | 2/2000 | Von Iderstein |
| 6,039,750 | A | * | 3/2000 | Kubalak et al. ............ 606/201 |
| 6,068,618 | A | | 5/2000 | Anderson |
| 6,131,575 | A | | 10/2000 | Lenker et al. |
| 6,131,576 | A | | 10/2000 | Davis |
| 6,138,678 | A | | 10/2000 | Nilsson |
| 6,171,231 | B1 | | 1/2001 | Connolly |
| 6,234,174 | B1 | | 5/2001 | Cheng et al. |
| 6,289,895 | B1 | * | 9/2001 | Cheng et al. ............... 128/885 |
| 6,371,950 | B1 | | 4/2002 | Roslansky et al. |
| 6,463,932 | B1 | | 10/2002 | Single et al. |
| 6,479,726 | B1 | | 11/2002 | Cole |

* cited by examiner

Primary Examiner—Michael A. Brown
(74) Attorney, Agent, or Firm—Woodard, Emhardt, Moriarty, McNett & Henry LLP

(57) ABSTRACT

An external incontinence device for use in male urinary incontinence. The device is easy to fasten and unfasten with one hand to selectively apply pressure against the urethra. In one embodiment, the device includes an outer strap, which overlaps itself through a gate, and locks in position at desired tension. A lever on the strap, which can be easily lifted to unfasten the strap, achieves release. Desired pressure is preferably applied against the urethra with an inner lining. The lining can be lifted to achieve pressure against the urethra by pressing a button. The button can be locked in position to achieve continence by either a groove or ridge mechanism or by a ballpoint pen ratchet mechanism. The pressure can be released by pressing and tilting the groove and ridge mechanism, or by pushing the ballpoint pen mechanism again. The present device preferably allows the user to void through the urethra without removal of the device.

23 Claims, 13 Drawing Sheets

EXTERNAL INCONTINENCE DEVICE

BACKGROUND OF INVENTION

1. Field of Invention

The present invention relates to a medical device. More particularly the invention relates to a device which can be used externally to prevent urinary incontinence in male subjects.

2. Description of the Related Art

Currently available devices for male urinary incontinence are cumbersome to use and need a lot of manual dexterity. Each time a voiding function is needed the device needs to be removed and afterwards replaced to prevent incontinence. This is a very involved and embarrassing process, particularly in public rest rooms. Current devices are difficult to retain in place and difficult to put on. They also need to be of different sizes for different individuals. Some of them use Velcro® hook and loop fasteners for fastening which when wet lose their ability to effectively fasten and stay together. Most devices need two hands to operate and take substantial time to undo the device in order to complete the act of urination and to then replace the device and retain it in place. Some of them have very complicated mechanisms for putting pressure on the urethra for urethral co-aptation. Some devices have a fixed pressure point.

Most prior inventions are based on the principle of compression of the entire shaft of the penis thereby presuming compression of the urethra. This principle does work, but not always effectively. In these devices, to increase pressure on the urethra there needs to be increased compression on the penis, which becomes uncomfortable and leads to frustration due to the fact that there is still some leakage of urine.

A device that will selectively compress the urethra is preferable. There are inventions which work in this manner, for example as suggested in U.S. Pat. No. 6,289,895; however, the pressure on the urethra in this device is provided by means of a constant elevation portion on the device just under the urethra. To increase the pressure, the device must be tightened circumferentially.

Devices that act as a cap on the front part of the penis simply do not work.

Device that use external catheters and collection bags are cumbersome to use and hard to keep in place.

Devices placed in urinary tracts are prone to infection and blockage.

A device that can cause direct pressure on the urethra, thereby resulting in better closure of the urethra, and a mechanism that can vary this pressure on the urethra, rather than circumferential pressure on the entire penile body, is preferable. In preferred features the device does not have to be removed, or loosened circumferentially to allow a voiding function, and can be operated with one hand. A device that allows this with a simple push of the button for opening and closing would be one ideal type.

None of the current inventions are seen to describe the instant invention as claimed. Thus, the present invention of an external incontinence device solving the aforementioned problem is desired.

SUMMARY OF THE INVENTION

The current invention provides a device for treatment of male urinary incontinence. In a preferred embodiment, the device is suitable for single hand operation. The device, when in place, can be activated by one hand. Preferably, the device has a one push, advance and lock and then one push release mechanism. As a preferred feature, the device does not have to be removed during the actuation or for each act of urination. The push on and push off function may be carried out by one hand without significant movement of the device or the hand. Embodiments of the present invention make it more appropriate for use in public places without causing undue embarrassment to the user. In one preferred embodiment, the device comprises an outer deformable strap with a mechanism for closing the strap and retaining it around the shaft in a generally circular shape. The strap is easy to adjust in size, and one size fits all. Preferably, the retaining strap mechanism can be released by simply lifting a release lever on the strap with one finger, which allows loosening of the strap for removal or readjustment of tension.

Another part of the device is an engaging mechanism. In one embodiment, it comprises a push button with one or more grooves and a tension clip powered by a spring. When the button is engaged in a closed position, a groove locks into the edge of an opening in the strap and the tension clip retains the button in place. When raised the mechanism presses against a lower portion of the penile shaft to compress the urethra. To release the button, the tension clip is pushed and the button tilted, allowing the button groove to release from the strap opening and allowing the button to move away from the penis and urethra to an open position. In an alternate embodiment, the engaging mechanism includes a push-on/push-off ratchet button.

Preferably, the engaging mechanism includes a soft, flexible liner. This lines a portion of the inner circumference of the outer strap between the button and the penile shaft, and can be flexibly moved up or down with movement of the button. The lining is partially fixed to the strap, and, in the area where it comes in contact with the push button, it is free to flexibly move up and down. Preferably, the liner is resiliently biased to move the button to a disengaged position. One example of a preferred material is soft silicone, which is readily tolerated by the skin.

For basic use the strap is fastened snugly around the shaft of the penis by placing the closing portion of the strap through the gate and locking it in place with the release lever. When the gate is on top of the shaft, the engaging mechanism or button will automatically be positioned adjacent the urethra at the bottom. The device is then ready for use. Pushing the button advances the button and the lining towards the urethra, and locks it in place by engaging a groove on the button with the edge of an opening in the strap. By locking the button in this position, it puts compression pressure on the urethra by elevating the silicon lining. The urethral walls will then close together and create functional closure of the urethra. The urethra thus will not permit any urine to flow through it, and achieve continence.

When the patient has an urge to urinate, he can simply push the button to disengage the mechanism, causing the button and liner to resiliently move away from the urethra. This will lead to opening of the urethra by moving away the silicon lining. The person can then carry out normal urination. When the act of urination is complete, the device can be reactivated by a simple push of the button. It is not necessary to remove the device completely.

Accordingly, it is a preferred object of embodiments of the invention to provide an external device for use in people with unwarranted urinary leakage. The device is mechanically sound and easy to use.

It is a preferred object of the invention to provide a simple to use device allowing one hand operation.

It is a further feature of the invention that the device does not have to be removed for the act of urination and can be selectively changed between open and closed positions with ease.

A preferred feature of the invention is to provide a more suitable material for use in contact with the skin around a sensitive organ such as the penis, which is more easily acceptable and less abrasive.

It is an object of this invention to provide a device that can be used with minimum effort, mostly in a non-noticeable manner, thereby preventing embarrassment and humiliation in public places, and to make life more tolerable and livable for people having a handicap of urinary incontinence.

Further objects, features and advantages of the present invention shall become apparent from the detailed drawings and descriptions provided herein.

DETAILED DESCRIPTION OF THE PREFERRED EMBODIMENTS

Figure 1:
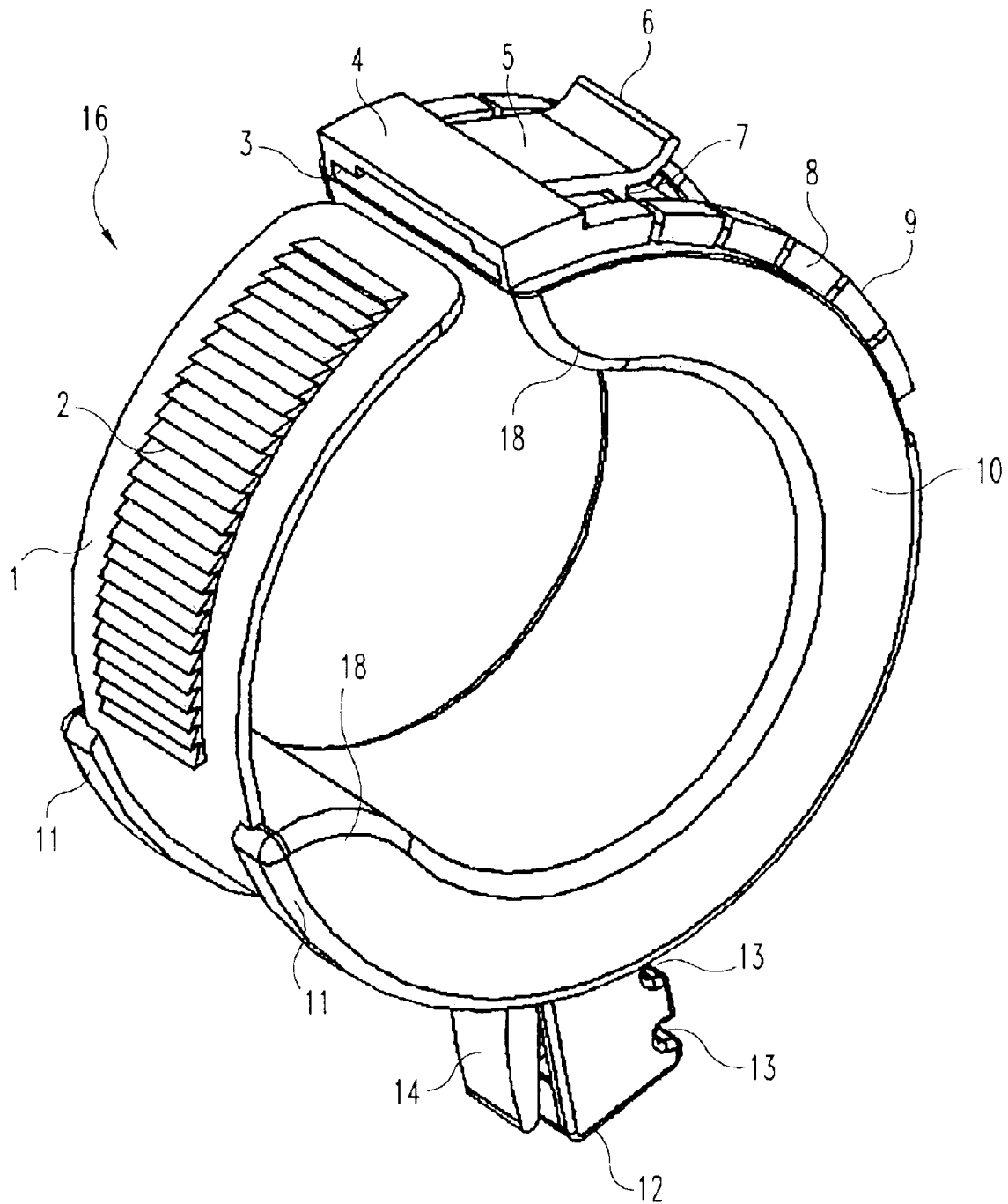
FIGS. 1–3 are perspective views of an external incontinence device according to a preferred embodiment of the present invention.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described device, and any further applications of the principles of the invention as described herein are contemplated as would normally occur to one skilled in the art to which the invention relates.

Figure 2:
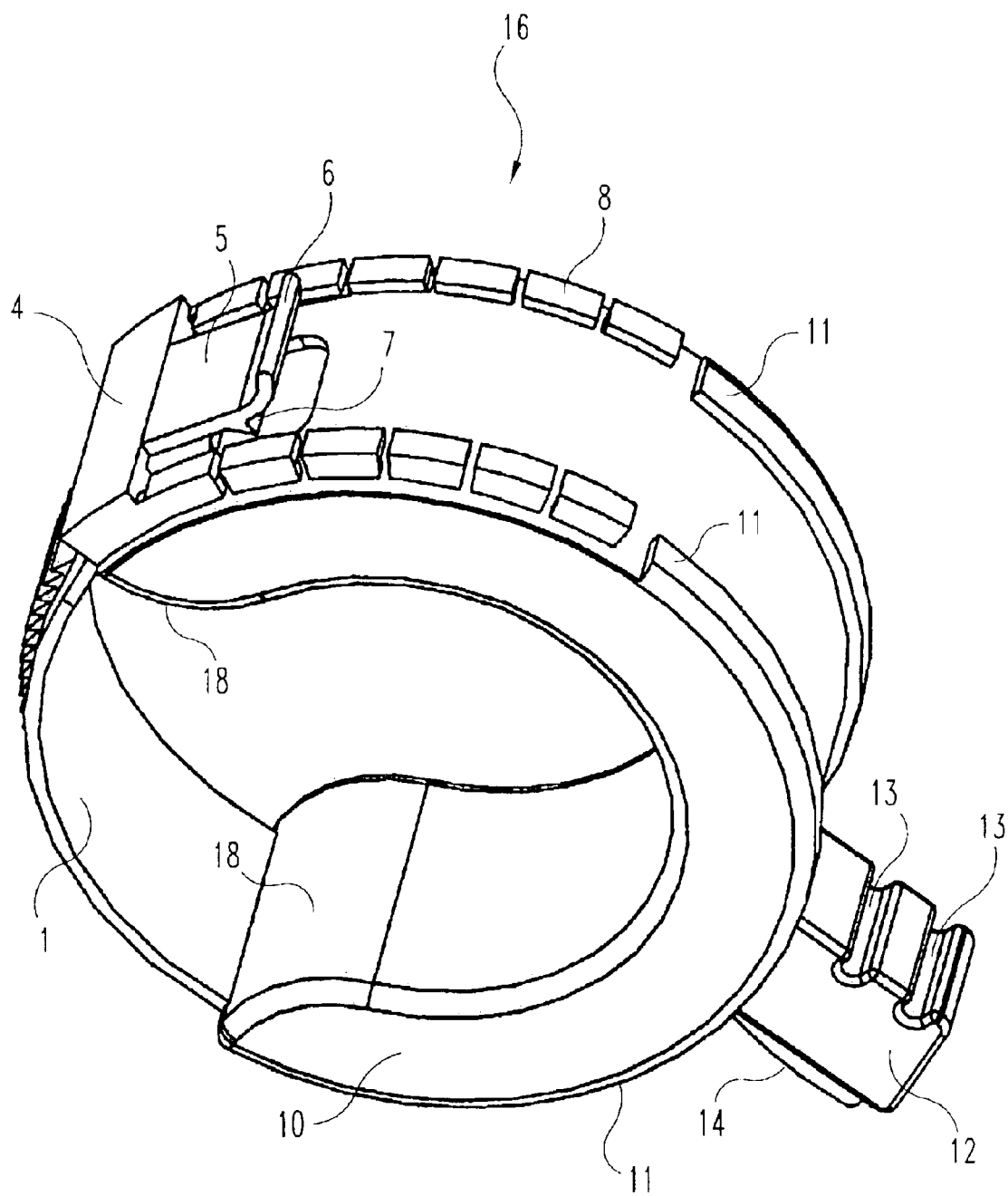
Figure 3:
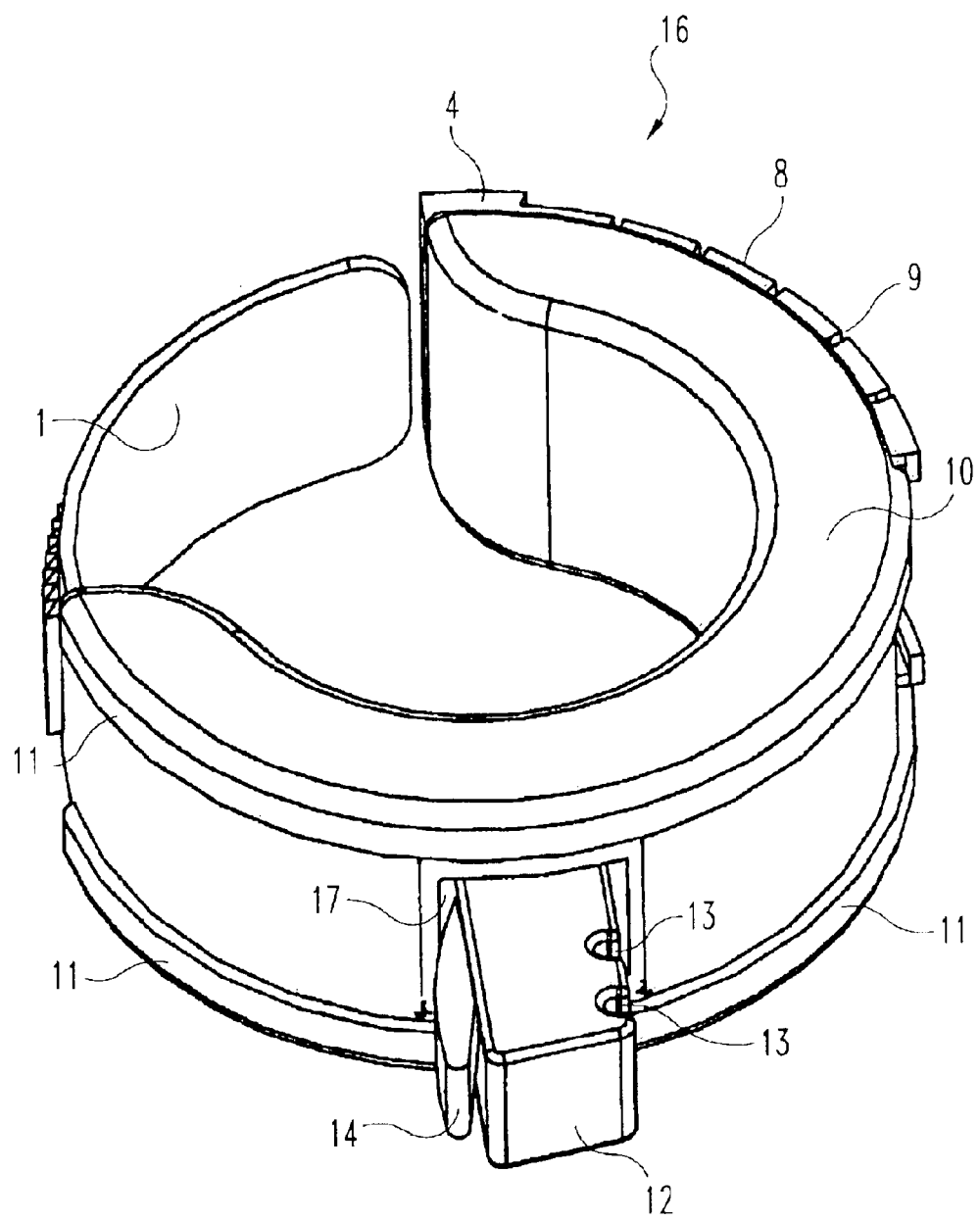

One embodiment of a preferred embodiment of the present invention is shown in FIGS. 1, 2, and 3. The external incontinence device 16 includes an outer strap 1 made of a deformable material such as plastic. In one example, the thickness of the strap 1 is between about 1 mm to 2 mm. The outer strap 1 is lined on the inside with a soft layer 10, such as silicon, covering approximately three-fourths of the strap 1 inner circumference. In one example the thickness of the silicon lining is between about 5 mm to 7 mm. The outer strap 1 accommodates the engaging mechanism 12 through an opening 17 on the lower side, opposite the strap locking mechanism.

In one embodiment, the outer strap 1 has a closing portion 2 with grooves and ridges on its outer surface in an area that is free from soft layer 10 on the inside. When the strap closing portion 2 is threaded through bracket 4 of gate 3, the grooves and ridges will pass under the lever 5, where a ridge 7 will lock into a groove on closing portion 2. This secures the strap 1 in a generally circular closed position. The strap's circumference can be adjusted as needed for comfort by selecting an appropriate groove. The gate 3 stabilizes the strap 1 in position and also helps maintain the shape of the device 16. The gate 3 also ensures smooth passage of closing portion 2 to a locked position, and prevents accidental unfastening. Side rails 8 and slits 9 are for stabilization of the strap on the sides and limit sideways movement of the strap closing portion. Alternate closing mechanisms, such as velcro, buckles, snaps or zippers are less preferred.

Unfastening of strap 1 from its circular closed position is easily achieved by lifting the edge 6 of the release lever 5. This maneuver lifts ridge 7 from the grooved portion of the strap 1 and releases closing portion 2, which then can be moved in a convenient direction either for tightening the device or for loosening or removing it.

Figure 4:
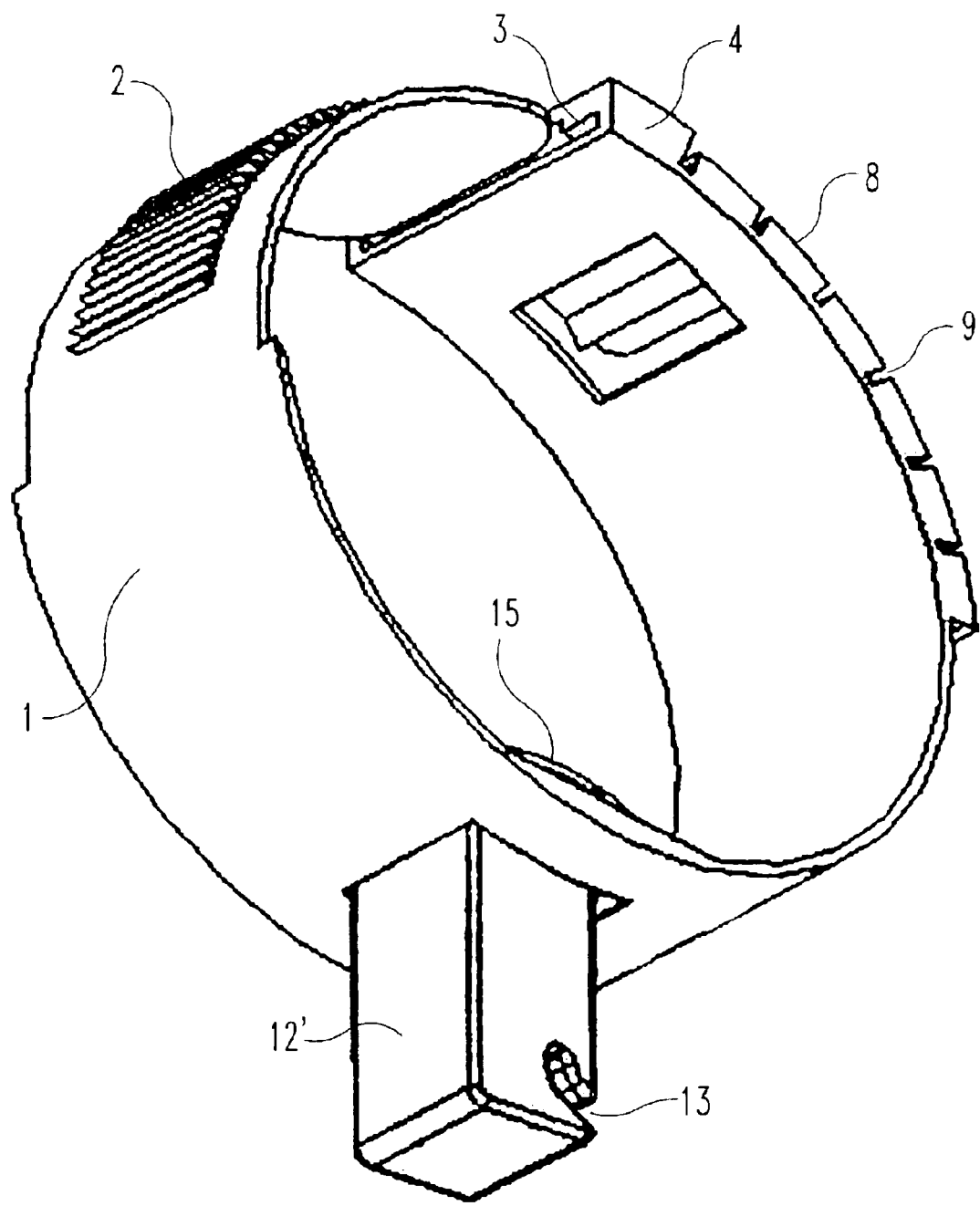
FIGS. 4 and 5 are alternative perspective views of the external incontinence device of FIG. 1 with an alternate engaging mechanism.
Figure 5:
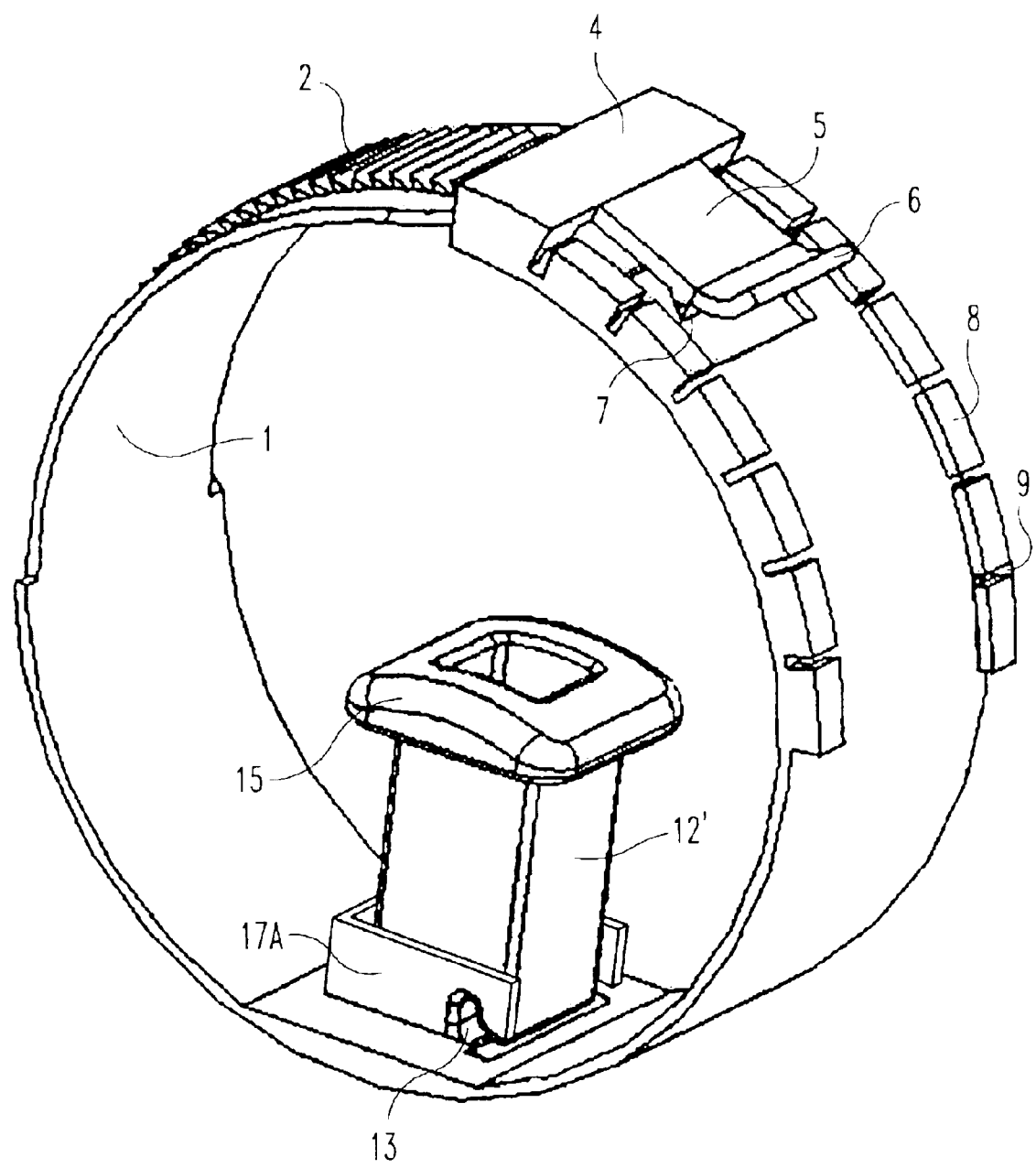

The strap 1 defines a lower opening 17 for the engaging mechanism, such as locking button assembly 12. A similar but alternate button assembly 12' with one groove is illustrated in FIGS. 4 & 5. The inner edge of opening 17 is framed by rails 17A (FIG. 5) on three sides, except the side where a groove 13 of push button 12 can lock with an opening edge. The rails 17A are positioned on the inside of strap 1 adjacent and within the lining, to stabilize and prevent a side to side or front to back movement of the push button assembly 12. The rails 17A assist in holding push button assembly 12 straight and keep it from tilting.

The inner lining 10 covers preferably about three-fourths of the inner circumference of the strap 1, and in one embodiment stops short of the grooved closing portion 2. When the device is tightened completely around a penis, the lining ends 18 come close together and form most of a complete circle around the penile shaft. The lining 10 is soft, pliable and tolerable by tissue and is comfortable to wear around the penile shaft. The lining 10 preferably has elastic properties and the edges 11 over-molded around the edges of the strap 1. In a preferred embodiment, the lining is made of silicone.

Figure 6:
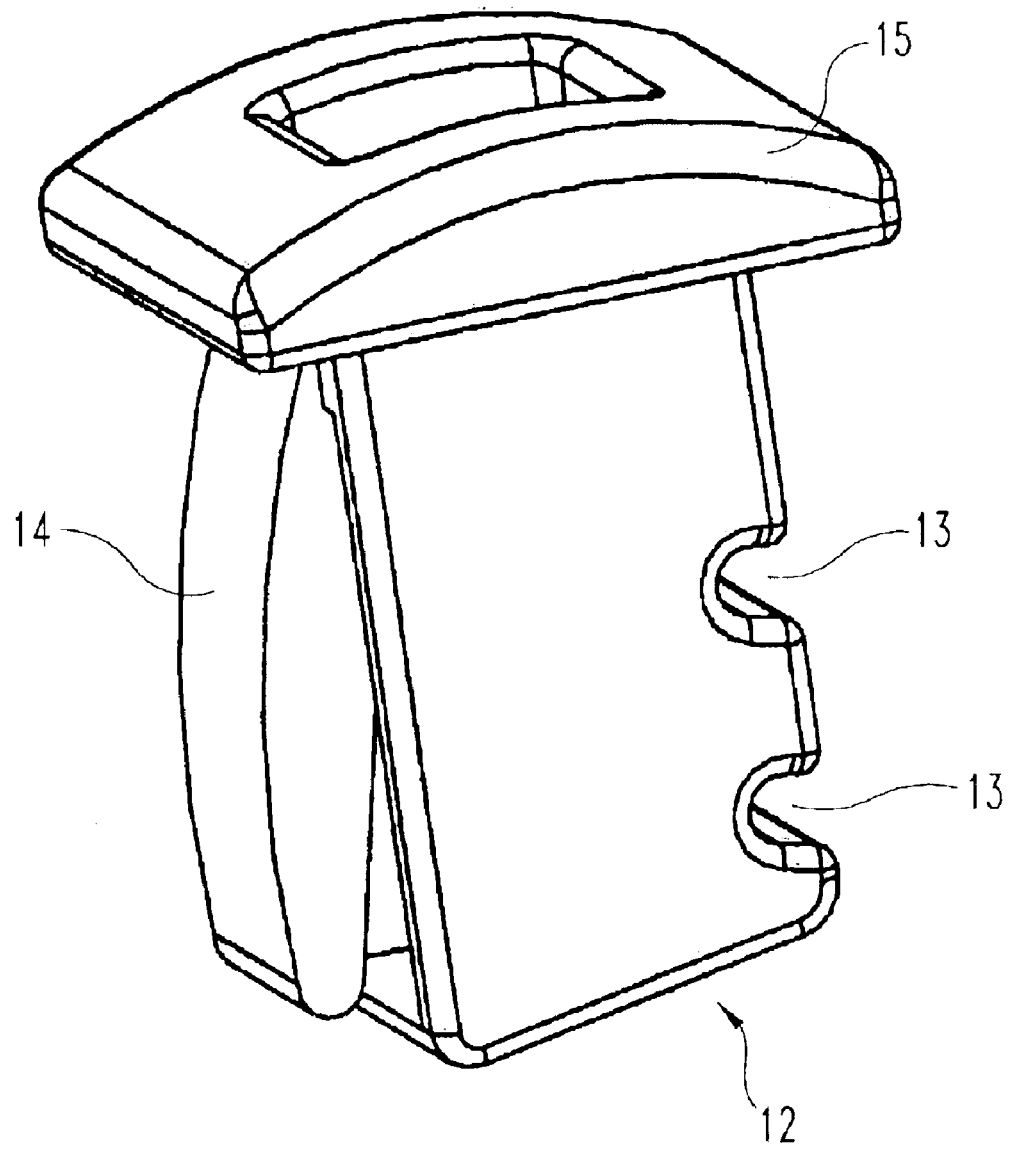
FIG. 6 is a perspective view of the engaging mechanism of FIGS. 1–3.
Figure 7:
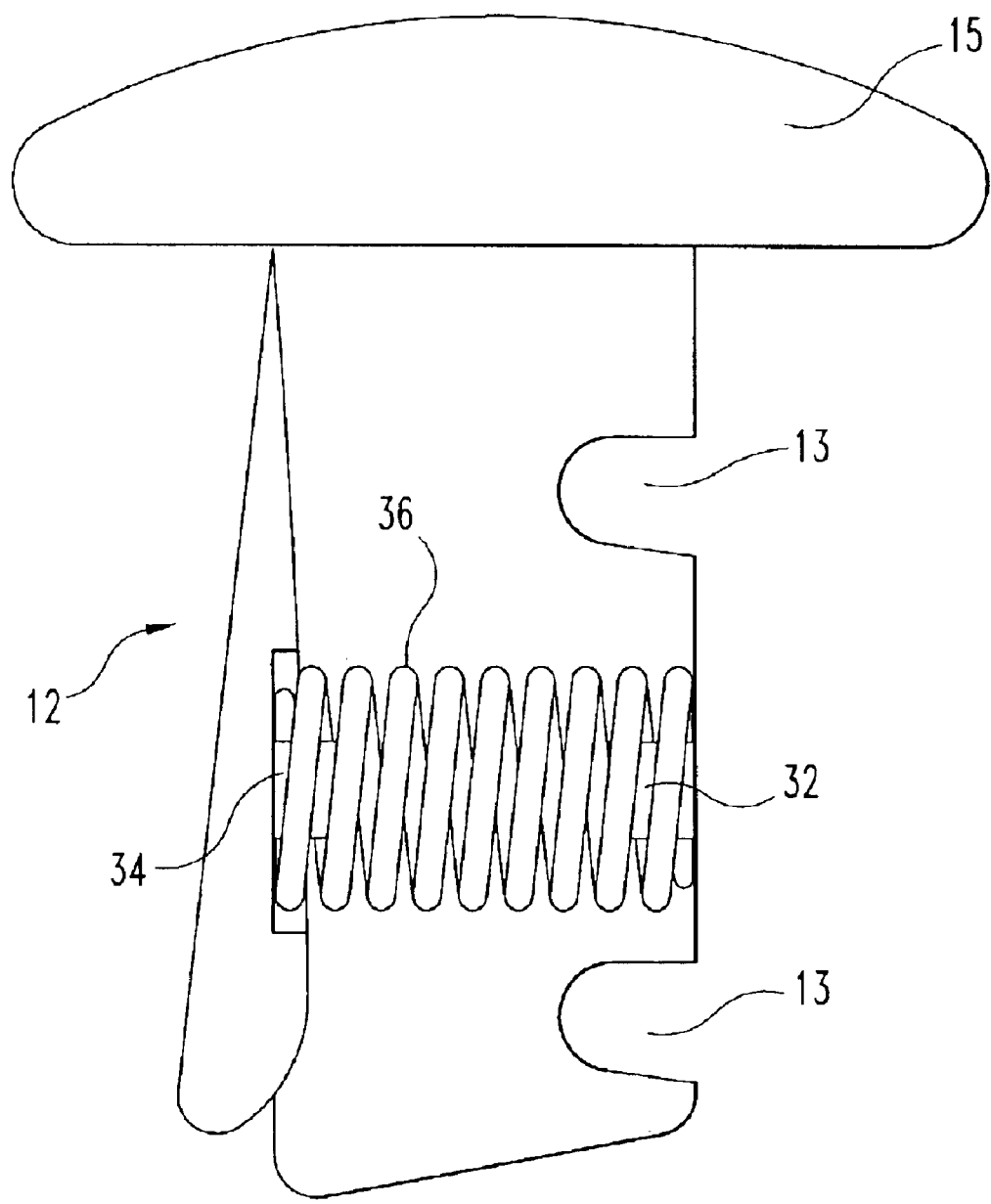
FIG. 7 is a cut-away view of the engaging mechanism of FIG. 6.

One embodiment of the engaging mechanism, such as button assembly 12 is shown in FIG. 6, with a cut-away view in FIG. 7. The locking of the button assembly 12 in the pushed up or closed position is further aided by tension clip 14 on the side of the button. Tension on the clip is maintained by a spring 36 inside the button. The spring sits on two opposing inside knobs 32 and 34. One knob 34 is on the side of the tension clip. The second knob 32 is on the side opposite the tension clip. These knobs prevent slippage of spring 36. When the button is advanced into the strap opening 17, the edges of the entrance (FIG. 5) apply pressure to tension clip 14. The inside spring 36 tension keeps the tension clip butted against the strap opening edge and also aids in securing a groove 13 into an opposing edge of the strap opening and locking the button in place. Over-molded edges 11 maintain downward pressure on the button 12, and biases the engaging mechanism to move away from the center when released. To release the button, a combination of upward pressure and side tilt towards the tension clip 14 is needed. This can be achieved by one finger. The button 12 will then move downward, releasing the pressure on the silicon lining 10, and allowing the urethra to open. Button 12 may have a convex or concave head 15 against the liner.

Figure 8A:
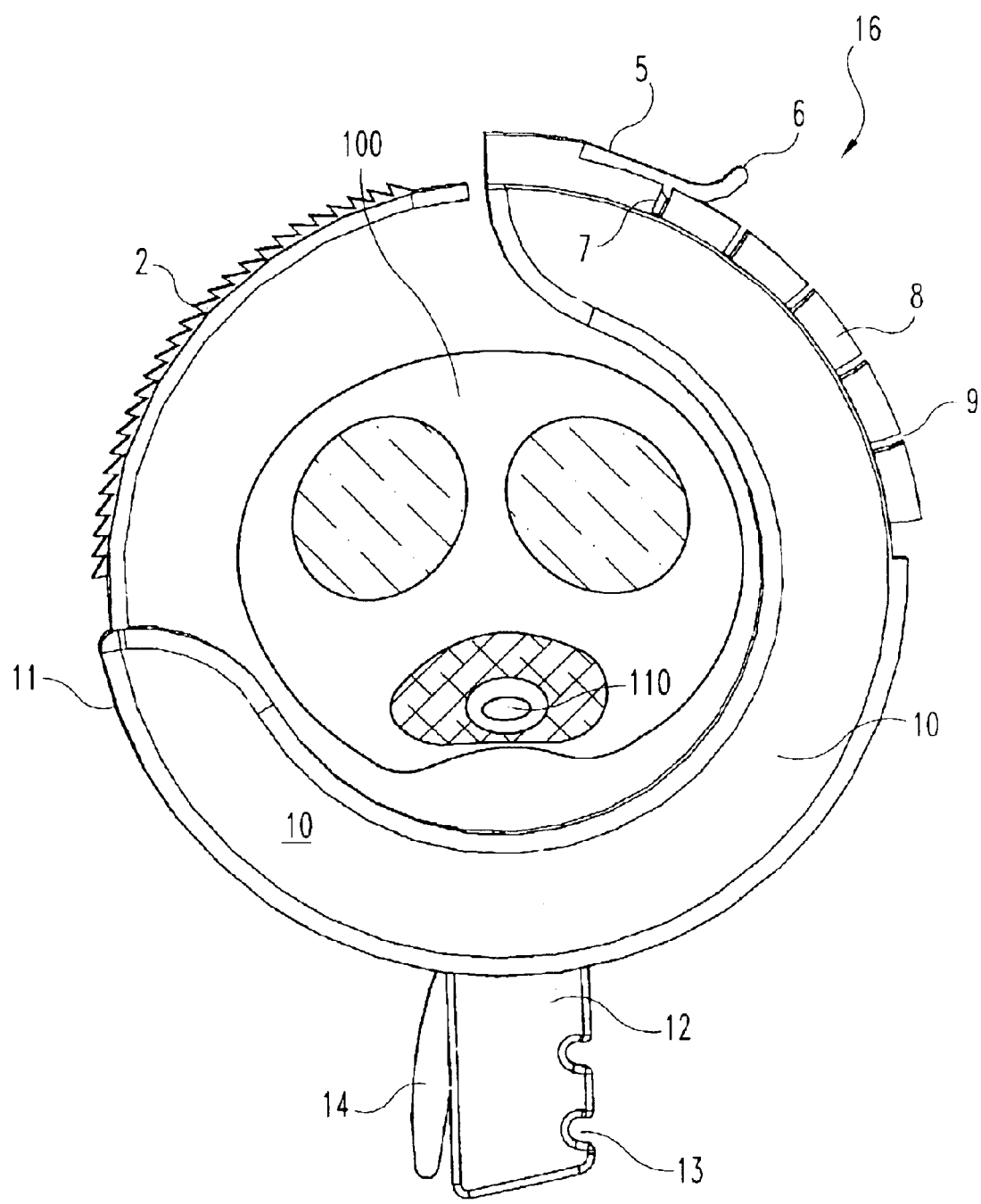
FIGS. 8A and 8B shows open and closed position of a preferred embodiment of the present invention around a penile shaft.

Open and closed operation of device 16 is shown in FIGS. 8A & B. To use the device 16, it is placed around the penile shaft 100 with the strap closing portion 2 outside the gate 3. Once in place, the closing portion 2 is passed through gate 3. It will automatically pass under lever 5 and ridge 7 and start locking. Closing portion 2 is advanced until device 16 is comfortably snug around the proximal most portion of the shaft. As the closing portion is advanced, as shown in FIG. 8B, the circumference of strap 1 is reduced.

Figure 8B:
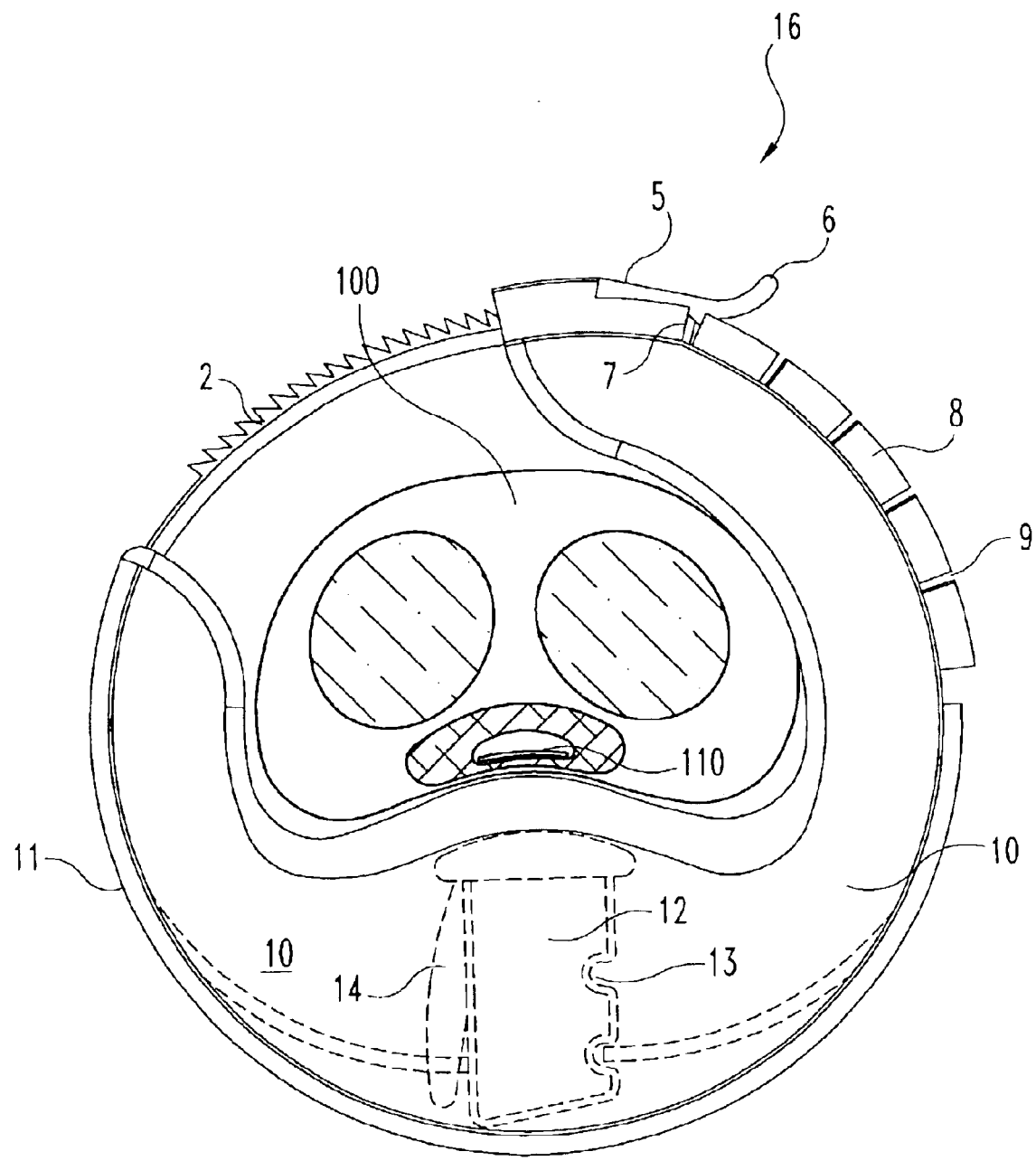
Figure 9:
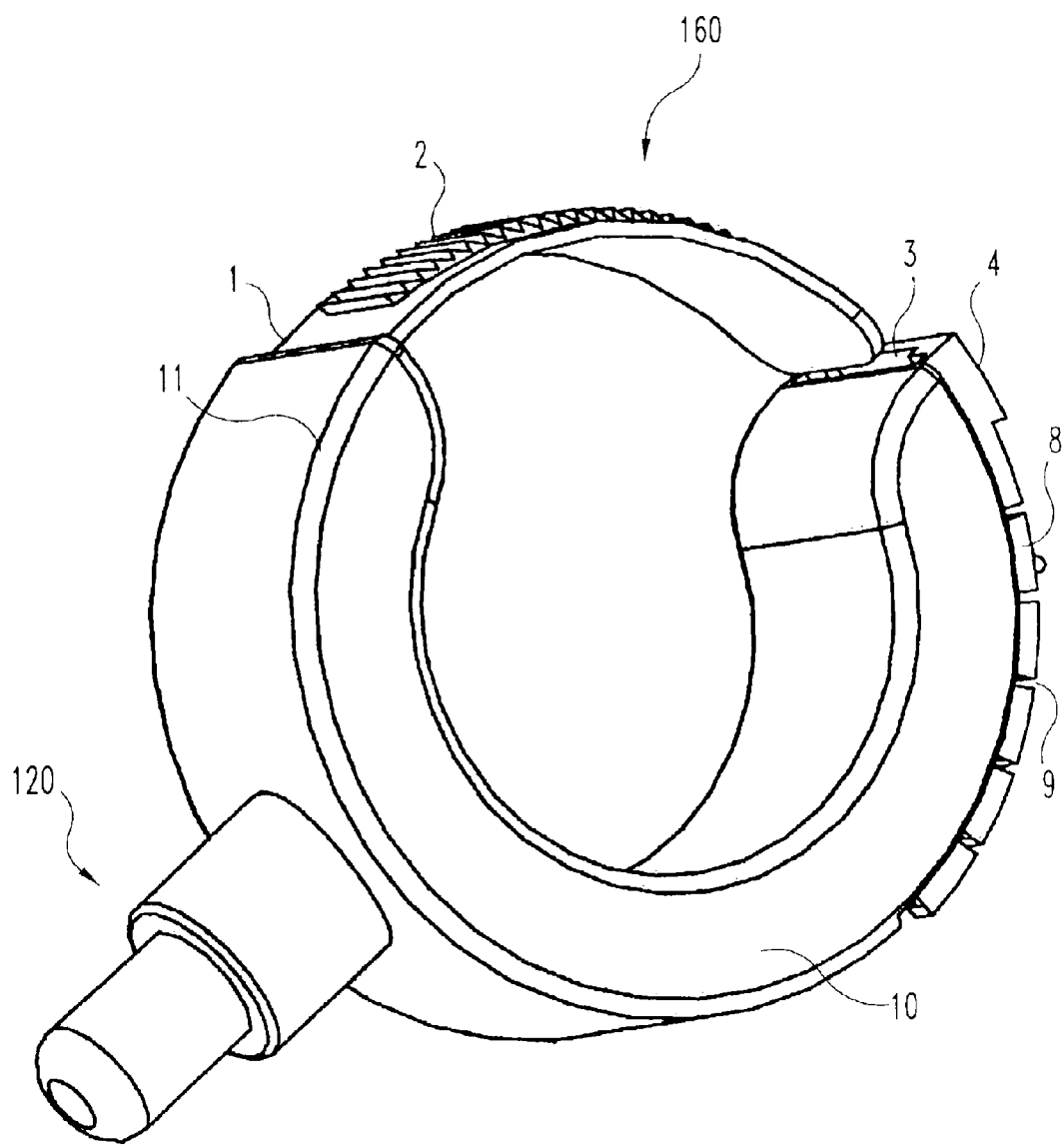
FIG. 9 shows a perspective of an alternate preferred embodiment of the present invention.

As illustrated in the closed position in FIG. 8B, when the button 12 is pushed upward through opening 17 in strap 1, the button plate 15 and lining 10 lift towards the center of the strap 1. Strap 1 does not lift or move. The lifted plate 15 and lining 10 push against the urethra 110 and makes it co-apt. This results in closure of the urethra, and thereby allows achieving of continence.

The pressure on the urethra can be varied by using one of the two grooves 13. If additional pressure is needed, the device can be further tightened by advancing the closing portion 2 of strap 1 further through the gate 3. The device can then be left in position, and, as long as the button stays in the locked position, the person will not have an undue leakage of urine.

To selectively close and open the urethra, it is not necessary to manipulate or remove the entire device 16. It is simply achieved by pushing the button once for closure and pushing the button again and tilting it for release/opening. When a person has a desire to void, pushing and titling the button will release pressure on the urethra 110 and allow him to urinate. When finished with the act of urination, he can simply push the button again to raise the button to prevent further leakage of urine.

The same effect of lifting the silicon and locking the button in an up position can be achieved by an alternate engaging mechanism, such as push-on/push-off ratchet mechanism 120, similar to a ballpoint pen, (shown in FIGS. 9–12) as shown in alternate embodiment 160. The push-button mechanism works much the same as the button with groove and ridge mechanism as far as its effect is concerned to elevate the silicon lining and when released to allow the lining to move away from the urethra. Pushing the button once elevates the silicon lining and holds it in a position against the penile shaft 100 to keep the urethra 110 closed. To move the silicon lining 10 away from the urethra, the button is pushed again to unlock and lower the plate and lining. The button locks in the open or closed position due to an internal mechanism similar to a ballpoint pen mechanism.

The internal working of the button is described in my previous U.S. Pat. No. 6,432,038 B1, issued Aug. 13, 2002 for an artificial urinary sphincter. The type of ratcheting and turning mechanism is well known and is illustrated in the retractable pen such as in U.S. Pat. No. 3,679,317, issued Jul. 25, 1972 to Ivar G. Larson, hereby incorporated by reference. Preferably the elastic properties of the lining obviate the need for a spring.

Figure 10:
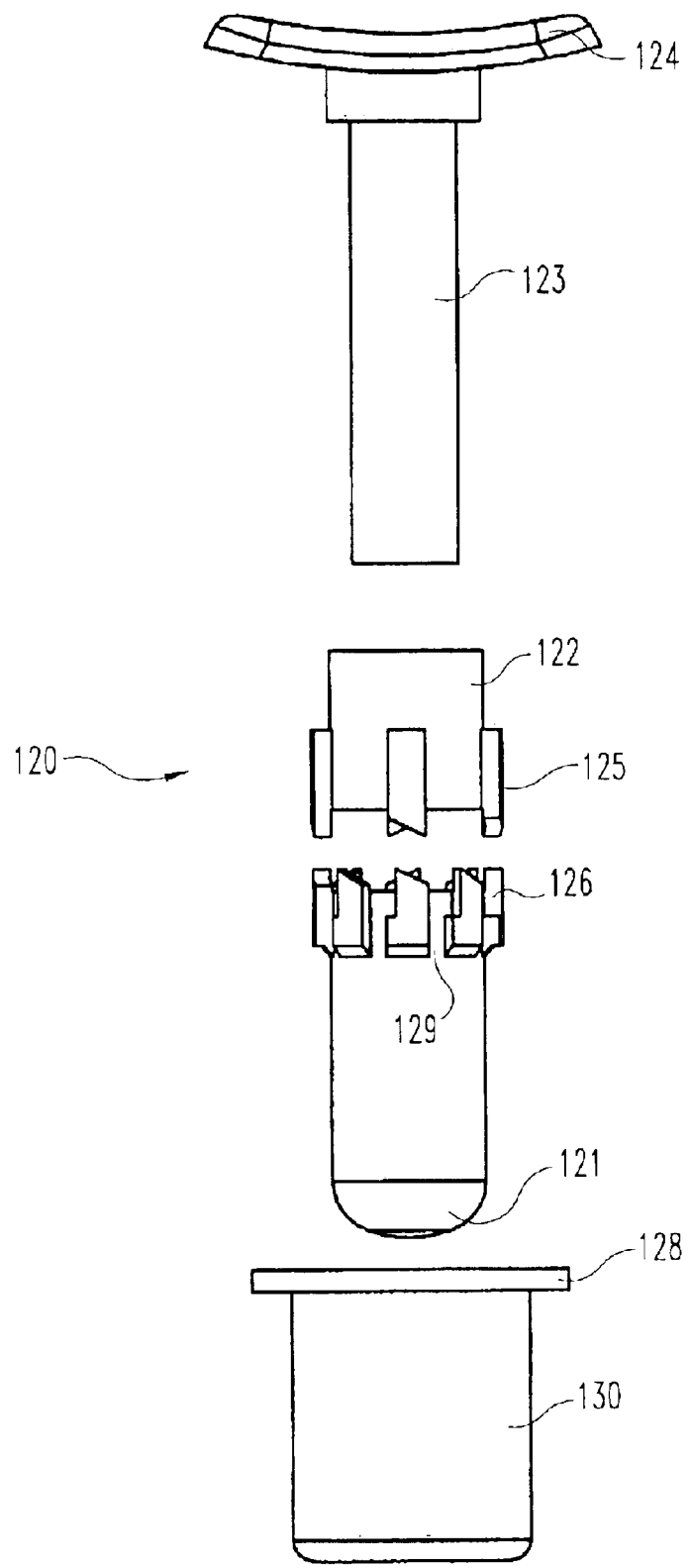
FIGS. 10–12 are views of the alternate engaging mechanism of FIG. 9.
Figure 11:
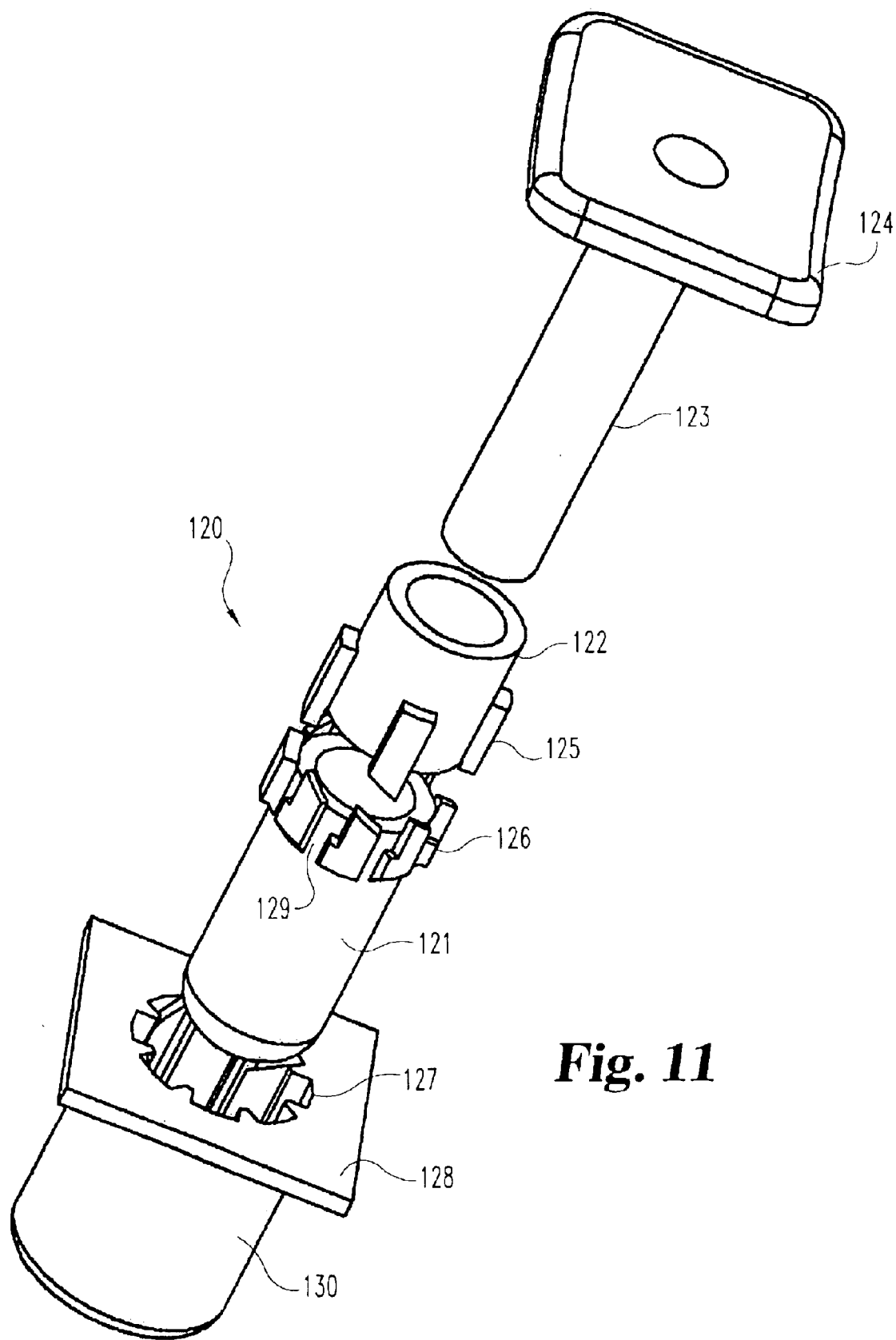
Figure 12:
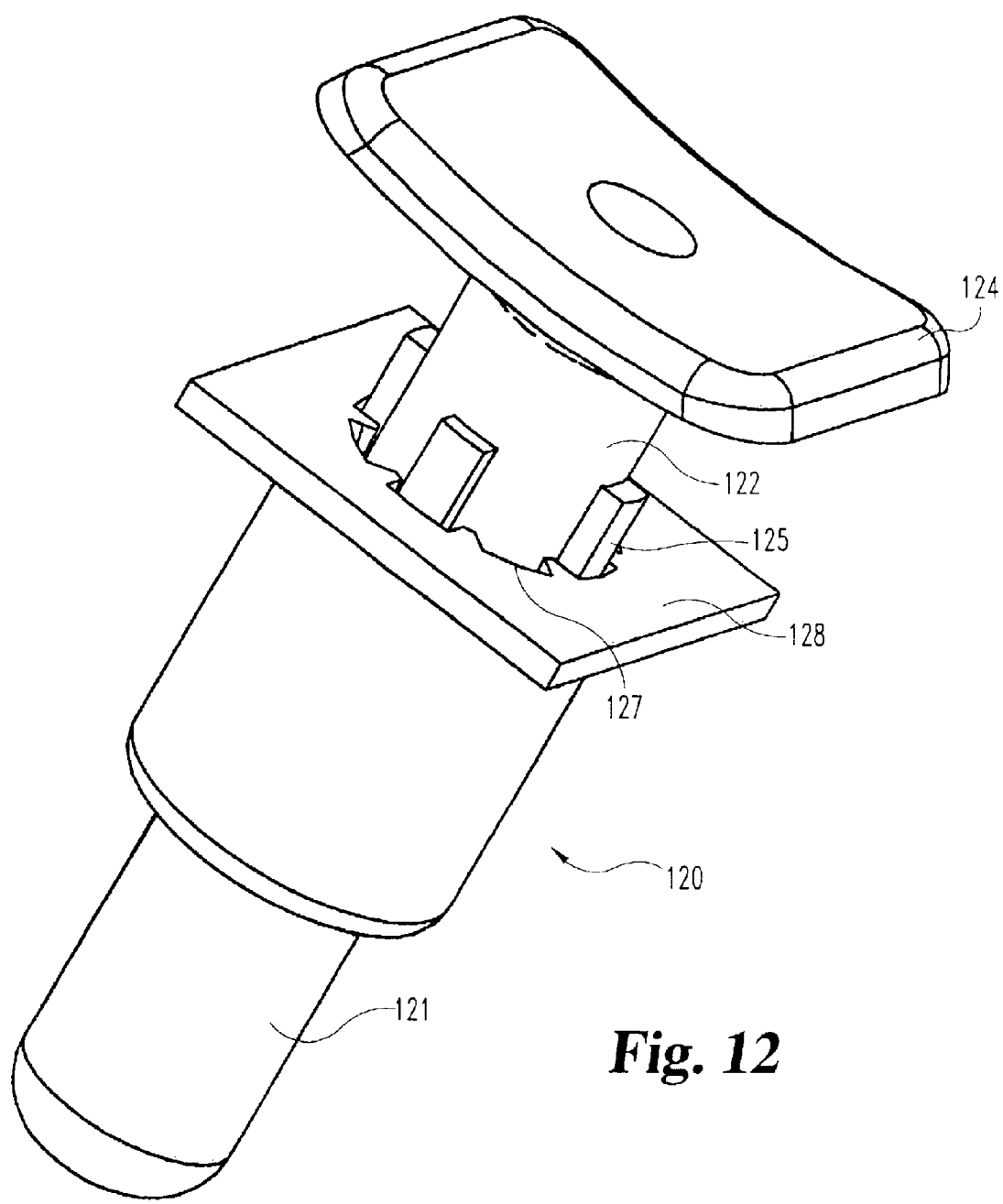

FIGS. 10–12 depict different views of the ratchet version of push-button mechanism 120. Mechanism 120 includes an outer base 130, and actual push button 121. Outer base 130 includes collar 128, actual push button 121 includes grooves 129 and ridges 126. Rotating collar 122 includes ridges 125. Elevator 123 includes elevator plate 124.

In assembled position, the push button mechanism 120 extends through opening 17 in strap 1 as shown in FIG. 1. The collar 128 on the base 130 butts against the inside of the opening 17 to retain the collar in position. The mechanism can alternately be held in place by a circular rail on the outer side of the strap to which the base is threaded. The opening 17 in the strap is preferably just large enough to accommodate the base 130. The collar 128 is wide enough to prevent the base 130 from sliding out of the strap opening. Preferably, use of a threaded mechanism eliminates the need for a collar on the outer base 130. The actual push button 121 fits inside the outer base 130. Ridges 126 on the actual button shaft 129 fit between ridges 127 in base 130.

On rotating collar 122, the ridges 125 engage grooves 129 on actual button 121, when the button is unlocked and the button is allowed to move downward. In the locked position, when the button is pushed up, the ridges 125 on rotating collar 122 engage ridges 126 on actual button 121. In this position the elevator 123 with its plate 124 is pushed up by the button and retained there to maintain pressure on the urethra to close it and achieve continence. When button 121 is pushed again, ridges 126 move down in the grooves 127 in base 130. Downward movement of button 121 allows elevator 124 to slide down, aided by pressure from the lining 10 due to its recoil and elasticity. Plate 124 may be concave or convex.

Suggested materials for the outer strap 1 are high impact plastic or similar suitable materials, alternate materials such as leather or cloth are less preferred. This material preferably is semi-flexible. Inner lining is preferably of silicon for its softness, ability to conform to penile shaft, and comfortable feel, although other materials such as rubber, foam or cloth may be used. The lining preferably also is able to generate enough downward pressure to release the button, due to its elasticity and ability to recoil. Preferably, the materials of the device are water resistant.

All publications, patents, and patent applications cited in this specification are herein incorporated by reference as if each individual publications, patent, or patent application were specifically and individually indicated to be incorporated by reference and set forth in its entirety herein. While the invention has been illustrated and described in detail in the figures and foregoing description, the same is to be considered as illustrative and not restrictive in character, it being understood that only the preferred embodiment has been shown and described and that all changes, equivalents, and modifications that come within the spirit of the invention as defined by the following claims are desired to be protected.

What is claimed is:

1. An external incontinence device for a penile shaft, comprising:
    a) a flexible strap having a closing portion at one end and a locking mechanism at the opposing end and an inner circumference therebetween;
    b) wherein said closing portion is selectively engagable with said locking mechanism for closing said strap to retain it around the penile shaft in a generally circular shape generally defining a circumference and a center;
    c) an engaging mechanism mounted to said strap and placed adjacent the urethra in the penile shaft;
    d) a silicone lining mounted along at least a portion of said inner circumference to cover at least said engaging mechanism;
    e) wherein said engaging mechanism is selectively movable from an open position adjacent the urethra and adjacent the strap to a closed position lifting a portion of said lining away from the strap circumference and towards the center of said strap to compress said lining against the urethra to achieve continence.

2. The device of claim 1, wherein said engaging mechanism comprises a push button assembly with a longitudinal axis oriented in a line towards the strap center and operable to raise said engaging mechanism towards the center of said strap.

3. The device of claim 2, wherein said push button assembly comprises a length with grooves formed to engage an opening in said strap.

4. The device of claim 2, wherein said push button assembly comprises a push-on/push-off ratchet mechanism.

5. The device of claim 2 wherein said lining is biased to urge said engaging mechanism to the open position.

6. The device of claim 5 wherein said closing portion comprises a grooved and ridged portion and wherein said locking member comprises a gate with a lever lockingly engagable with said grooved and ridged portion.

7. An external incontinence device for a penile shaft, comprising:
   a) a flexible strap;
   b) a mechanism for closing said strap to retain it around the penile shaft in a generally circular shape generally defining a circumference and a center;
   c) an engaging mechanism mounted to said strap and placed adjacent the urethra in the penile shaft; and
   d) wherein said engaging mechanism includes a movable portion selectively movable from an open position adjacent the urethra to a closed position lifted away from the circumference of said strap and towards the center of said strap and compressing the urethra to achieve continence.

8. The device of claim 7 wherein said mechanism for closing said strap comprises a grooved and ridged closure portion adjacent one end of said strap, and wherein said grooved and ridged closure portion is engagable with a gate at the opposing end of said strap.

9. The device of claim 7 wherein said engaging mechanism comprises a lining mounted to at least a portion of the inner circumference of said strap, situated to be at least between the movable portion of said engaging mechanism and the penile shaft.

10. The device of claim 9 wherein said engaging mechanism further comprises a push button assembly mounted through an opening defined in said strap and selectively movable against said lining to operate said engaging mechanism between the open position and the closed position.

11. The device of claim 10 wherein said push button assembly includes a length with at least one groove engagable with an edge of said strap opening to retain said push button assembly in the closed position.

12. The device of claim 11 wherein said push button assembly further comprises a clip mounted to said length opposing said grooves and biased against said opening to retain said push button assembly in the closed position.

13. The device of claim 11 wherein said length of said push button assembly defines two grooves.

14. The device of claim 13 further comprising a frame around said strap opening.

15. The device of claim 10 wherein said push button assembly comprises a push-on/push-off ratchet mechanism.

16. The device of claim 9 wherein said push button assembly comprises,
   a) a base mounted to said strap;
   b) a push button operable through said base;
   c) a rotating collar engaged by said push button; and,
   d) a plate adjacent said lining.

17. The device of claim 16 wherein said base of said push button assembly is in threaded engagement with a collar mounted to said strap.

18. The device of claim 9 wherein said lining is formed of silicone.

19. The device of claim 9 wherein the edges of said lining overlap the edges of said strap.

20. The device of claim 19 wherein said lining is elastic and biased to urge said engaging mechanism to the open position.

21. A method for applying an external incontinence device to compress the urethra in a penile shaft, comprising:
   a) placing a flexible strap around the penile shaft;
   b) placing an engaging mechanism adjacent the urethra on the lower portion of the penile shaft;
   c) closing said strap around the penile shaft in a generally circular shape defining a fixed circumference;
   d) selectively lifting said mechanism against the lower portion of the penile shaft from an open position adjacent said circumference to a closed position raised towards the center of said shape of said strap relative to said circumference, thereby compressing the urethra to achieve continence; and,
   e) placing a soft lining between said engaging mechanism and the urethra, wherein said engaging mechanism raises said lining away from the circumference of said strap and towards the center of said strap when lifting the engaging mechanism to the closed position.

22. The method of claim 21 further comprising the step of closing said strap snugly around a portion of the penile shaft to retain the device in position.

23. The method of claim 21, further comprising the step of lowering said lining towards the strap circumference when moving said engaging mechanism to the open position.

* * * * *